United States Patent [19]

Petruck et al.

[11] 4,107,186
[45] Aug. 15, 1978

[54] 4-HYDROXYANTHRONES AND PROCESS OF PREPARATION

[75] Inventors: Gerd-Michael Petruck, Bergisch-Gladbach; Erich Klauke, Odenthal-Hahnenberg; Horst Jäger, Leverkusen, all of Germany

[73] Assignee: Bayer Aktiengesellschaft, Leverkusen, Germany

[21] Appl. No.: 858,035

[22] Filed: Dec. 6, 1977

[30] Foreign Application Priority Data

Dec. 9, 1976 [DE] Fed. Rep. of Germany ....... 2655824
May 24, 1977 [DE] Fed. Rep. of Germany ....... 2723350

[51] Int. Cl.² .............................................. C07C 49/82
[52] U.S. Cl. ..................................... 260/351; 260/333
[58] Field of Search ......................... 260/351, 333, 336

[56] References Cited

U.S. PATENT DOCUMENTS 3,420,868   1/1969   Weil ..................................... 260/463
3,835,167   9/1974   Pfister .................................. 260/351

FOREIGN PATENT DOCUMENTS 370,037   3/1932   United Kingdom .................... 260/351

Primary Examiner—Allen B. Curtis
Assistant Examiner—Raymond K. Covington
Attorney, Agent, or Firm—Burgess, Dinklage & Sprung

[57] ABSTRACT

4-Novel hydroxyanthrones of the formula

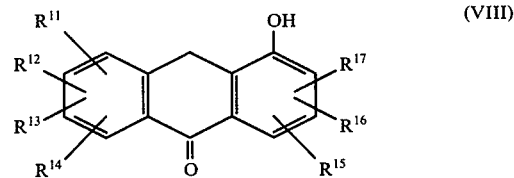

wherein $R^{11}$ and $R^{17}$ are as set forth in the specification.

and a process for the preparation of 4-hydroxyanthrones wherein (2-halogeno-methyl)-phenyl haloformates of the formula

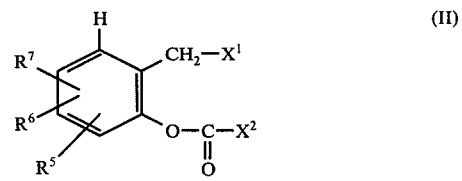

wherein $R^5$-$R^7$ are as set forth in the specification are reacted, with an aromatic carbocyclic compound of the formula

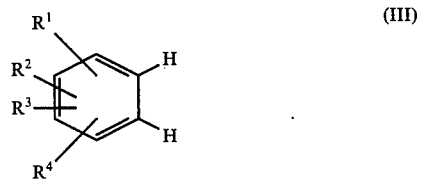

wherein $R^1$ to $R^4$ are as set forth in the specification in the presence of a Friedel-Crafts catalyst, optionally in a solvent, at a temperature in the range of from 0° to 300° C.

10 Claims, No Drawings

4-HYDROXYANTHRONES AND PROCESS OF PREPARATION

The invention relates to a process for the preparation of 4-hydroxyanthrones.

A process has been found for the preparation of 4-hydroxyanthrones of the formula $$\text{(I)}$$

wherein $R^1$ to $R^7$ are identical or different and denote hydrogen, hydroxyl, halogen, cyano, $C_1$-$C_4$-alkyl, $C_1$-$C_4$-alkoxy, $C_1$-$C_4$-alkylmercapto, $C_1$-$C_4$-alkylsulphonyl, trifluoromethyl, trichloromethyl or an amino group of the formula $$-N\begin{smallmatrix}R^8\\R^9\end{smallmatrix}$$

wherein $R^8$ and $R^9$ are identical or different and represent hydrogen, $C_1$-$C_4$-alkyl or $C_1$-$C_4$-alkylcarbonyl, in which (2-halogeno-methyl)-phenyl haloformates of the formula $$\text{(II)}$$

wherein $R^5$ to $R^7$ have the meaning indicated above and $X^1$ and $X^2$ are identical or different and represent halogen, are reacted, or intermediate products obtainable by reacting the compounds of formulae (II) and (III) are reacted, with an aromatic carbocyclic compound of the formula $$\text{(III)}$$

wherein $R^1$ to $R^4$ have the meaning indicated above, in the presence of a Friedel-Crafts catalyst, optionally in a solvent, in the temperature range from 0° to 300° C.

The process according to the invention can be illustrated by the following reaction equation for the reaction of (2-chloro-methyl)-phenyl chloroformate with benzene:

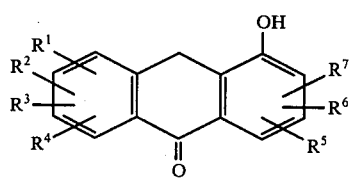

Halogen radicals ($X^1$ and $X^2$) can be fluorine, chlorine or bromine, preferably fluorine and chlorine.

$C_1$-$C_4$-Alkyl radicals ($R^1$ to $R^7$ and $R^8$ and $R^9$) can be methyl, ethyl, propyl, iso-propyl, butyl and isobutyl, preferably methyl and ethyl.

$C_1$-$C_4$-Alkoxy radicals ($R^1$ to $R^7$) can be methoxy, ethoxy, propoxy, iso-propoxy, butoxy and iso-butoxy, preferably methoxy and ethoxy.

$C_1$-$C_4$-Alkylmercapto radicals ($R^1$ to $R^7$) can be methylmercapto, ethylmercapto, propylmercapto, iso-propylmercapto, butylmercapto and iso-butylmercapto, preferably methylmercapto and ethylmercapto.

$C_1$-$C_4$-Alkylsulphonyl radicals ($R^1$ to $R^7$) can be methylsulphonyl, ethylsulphonyl, propylsulphonyl, iso-propylsulphonyl, butylsulphonyl and iso-butylsulphonyl, preferably methylsulphonyl and ethylsulphonyl.

$C_1$-$C_4$-Alkylcarbonyl radicals ($R^8$ and $R^9$) can be methylcarbonyl, ethylcarbonyl, propylcarbonyl, iso-propylcarbonyl, butylcarbonyl and iso-butylcarbonyl, preferably methylcarbonyl and ethylcarbonyl.

Halogen ($R^1$ to $R^7$) can be fluorine, chlorine, bromine or iodine, preferably fluorine, chlorine and bromine. Preferred (2-halogeno-methyl)-phenyl haloformates are compounds of the formula $$\text{(IV)}$$

wherein $R^{7'}$ denotes hydrogen, fluorine, chlorine, bromine, methyl, ethyl, methoxy or ethoxy, and $X^{1'}$ and $X^{2'}$ are identical or different and represent fluorine or chlorine.

The preparation of the (2-halogeno-methyl)-phenyl haloformates is known (U.S. Pat. No. 3,420,868). They can be carried out, for example, by halogenating o-cresyl haloformates with customary halogenating agents. (2-Halogeno-methyl)-phenyl haloformates which may be mentioned are, for example: 6-chloro-2-chloromethyl-phenyl chloroformate, 5-chloro-2-chloromethyl-phenyl chloroformate, 2-chloromethylphenyl chloroformate and 2-chloromethylphenyl fluoroformate. Aromatic carbocyclic compounds of the formula

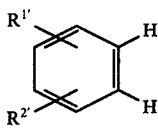

(V)

wherein $R^{1'}$ and $R^{2'}$ are identical or different and denote hydrogen, fluorine, chlorine, bromine, methyl, ethyl, methoxy or ethoxy, are preferred.

Aromatic carbocyclic compounds are known (Houben Weyl, volume IV/3, 1/1965 + volume IX, 93 (1955) + volume V, 551 (1962)).

The following aromatic carbocyclic compounds may be mentioned as examples: benzene, toluene, p-, m- or o-xylene, anisole, p-chloroanisole and 1,4-dimethoxybenzene.

All the catalysts which are customary for Friedel-Crafts reactions can be used as the Friedel-Crafts catalysts (Olah, Friedel-Crafts Chemistry (1973) New York).

Examples which may be mentioned are aluminum trichloride, antimony pentachloride, antimony pentafluoride, hydrogen fluoride, titanium tetrachloride, tin tetrachloride and iron trichloride and preferably aluminum trichloride, hydrogen fluoride and antimony pentachloride.

All the customary solvents which are inert under the reaction conditions can be used as the solvent or diluent. Chlorobenzenes, such as chlorobenzene, o-, m- or p-chlorotoluene and o-, m- or p-dichlorobenzene, and nitrobenzenes, such as nitrobenzene, o-, m- or p-nitrotoluene and o-, m- or p-dinitrobenzene, and nitromethane may preferably be mentioned. Chlorobenzene and nitromethane are particularly preferred as the solvent or diluent. It is, of course, also possible to use the aromatic carbocyclic compound, employed as the reactant, in excess or to employ a mixture of different solvents.

The process according to the invention is carried out in the temperature range from about 0° to about 300° C. The preferred temperature range is largely dependent on the compounds employed and on the reaction medium. If the process is carried out without a solvent, a temperature from about 100° to 250° C is in general preferred for the reaction. If the process is carried out in the presence of a chlorobenzene as the solvent, a temperature from about 80° to about 180° C is in general preferred. In the case where a nitrobenzene or nitromethane is used as the solvent, a temperature range from about 40° to about 100° C is in general preferred.

The process according to the invention can be carried out both under normal pressure and under increased pressure. The process is preferably carried out in the pressure range from 0.5 to 2 bars.

The process according to the invention can be carried out as follows:

An excess of the aromatic carbocyclic compound, optionally in a solvent or condensing agent, and the Friedel-Crafts catalyst are initially introduced into the reaction vessel and the (2-halogeno-methyl)-phenyl haloformate is added slowly at the reaction temperature. After the first part of the reaction was ended, the excess aromatic carbocyclic compound is distilled off and, if appropriate, further Friedel-Crafts catalyst is added and the reaction is brought to completion in solution or in the pure undiluted state. The Friedel-Crafts catalyst is then decomposed in the customary manner, for example by adding hydrochloric acid. The 4-hydroxyanthrone formed precipitates under the reaction conditions and, if necessary, can be purified in the customary manner, for example by recrystallising from alcohol or boiling up in toluene. If the reaction is carried out in solution, the oxepinone which is formed in certain circumstances and which is not completely rearranged remains in solution and can thus be easily separated off.

In a particular embodiment of the process according to the invention, one can prepare 4-hydroxyanthrone from the (2-halogeno-methyl)-phenyl haloformate and the aromatic carbocyclic compound in 3 reaction stages.

This embodiment is characterised in that, in a first reaction stage in the temperature range from 0° to 100° C, a 2 benzyl-phenyl haloformate of the formula

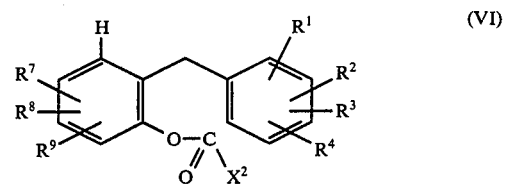

(VI)

wherein $R^1$ to $R^7$ and $X^2$ have the abovementioned meaning, is obtained by reacting the (2-halogeno-methyl)-phenyl haloformate with the aromatic carbocyclic compound, this haloformate of the formula (VI) is converted, in a second reaction stage, to a 11-H-dibenz[b,e]oxepin-6-one of the formula

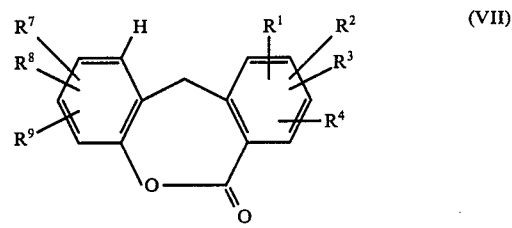

(VII)

wherein $R^1$ to $R^7$ have the abovementioned meaning, in the presence of a Friedel-Crafts catalyst, optionally in a solvent, at a temperature range from 20° to 120° C, and then, in a third reaction stage, the 11-H-dibenz[b,e]oxepin-6-one is rearranged in the presence of a Friedel-Crafts catalyst, optionally in a solvent, in the temperature range from 20° C to 300° C.

After each individual reaction stage has ended, the corresponding intermediate product can be isolated. It is, of course, also possible to employ, in the process according to the invention, the 2-benzyl-phenyl haloformate of the first stage or the 11-H-dibenz[b,e]oxepin-6-one of the second stage, which can optionally also be prepared in another manner, instead of the starting components.

It can be appropriate to carry out the process according to the invention and the working up in the presence of a protective gas, such as nitrogen or helium.

The following 4-hydroxyanthrones, which can be prepared by the process according to the invention, of the formula

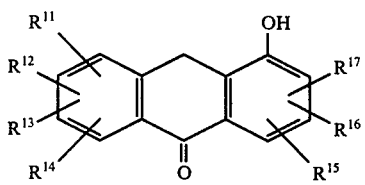 (VIII)

wherein $R^{11}$ to $R^{17}$ are identical or different and denote hydrogen, hydroxyl, fluorine, chlorine, bromine, cyano, $C_1-C_4$-alkyl, $C_1-C_4$-alkoxy, $C_1-C_4$-alkylmercapto, $C_1-C_4$-alkylsulphonyl, trifluoromethyl, trichloromethyl or an amino group of the formula

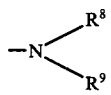

wherein $R^8$ and $R^9$ are identical or different and represent hydrogen, $C_1-C_4$-alkyl or $C_1-C_4$-alkylcarbonyl, at least one of the radicals $R^{11}$ to $R^{17}$ being different from hydrogen or methyl, are new.

Particularly preferred new 4-hydroxyanthrones are compounds of the formula

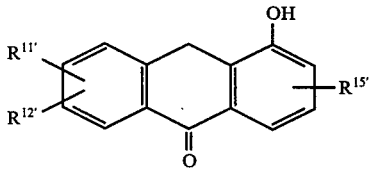 (IX)

wherein $R^{11'}$, $R^{12'}$ and $R^{15'}$ are identical or different and denote ethyl, methoxy, ethoxy, fluorine, chlorine or bromine.

The following 4-hydroxyanthrones may be mentioned as examples: 1,3-dimethyl-5-hydroxyanthrone, 1,4-dimethyl-5-hydroxyanthrone, 1,3-dimethoxy-5-hydroxyanthrone, 1-ethoxy-5-hydroxyanthrone, 1-bromo-5,8-dimethoxy-4-hydroxyanthrone, 3-chloro-4-hydroxyanthrone and 2-chloro-4-hydroxyanthrone.

Compared with the known method for the preparation of 4-hydroxyanthrone (JACS 52, 4887 to 4892 (1930)), the process according to the invention has a number of advantages. Thus, surprisingly, by the process according to the invention one can prepare 4-hydroxyanthrone in a simple manner, in higher yields than are possible by reacting phthalic anhydride and phenol.

The 4-hydroxyanthrones which can be prepared by the process according to the invention can be employed as intermediate products for vat dyestuffs see German Patent Specification No. 932,924, the disclosure of which is hereby incorporated herein by reference. For this purpose substituted or unsubstituted 4-hydroxyanthrones are reacted with glyoxal sulfate in basic or acidic solvents (e.g. pyridine/piperidine or acetic acid) in a temperature range of about 100°–120° C to yield vat dyestuffs of blue to green colour. Those dyestuffs have high boiling and bleaching resistance against soda and chlorine.

EXAMPLE 1

20.5 g (0,1 mol) of (2-chloromethyl)-phenyl chloroformate are added dropwise to 26.7 g (0.2 mol) of aluminum trichloride in 156 g (2 mols) of boiling benzene. The mixture is subsequently allowed to react for 1 hour at 80° C and 100 ml of o-dichlorobenzene are then added. The benzene is distilled off and the reaction mixture is warmed. The reaction, which is strongly exothermic from 80° C, is allowed to go to completion at temperatures up to 162° C. After cooling, the mixture is hydrolysed with 5% strength by weight hydrochloric acid and the product which has precipitated is filtered off. Yield: 19 g of 4-hydroxyanthrone (which corresponds to a yield of 90.5% of the theoretical conversion), melting point: 232° to 235° C; purity: 99.3%.

EXAMPLE 2

A mixture of 24.7 g (0.1 mol) of 2-benzylphenyl chloroformate and 13.5 g (0.1 mol) of aluminum trichloride is warmed. After the strongly exothermic reaction has started, at about 80° C, the reaction is carried out so that it goes to completion at 170° C (end of the evolution of gas). After the hydrolysis with 100 ml of 5% strength by weight hydrochloric acid, the solid which has precipitated is filtered off. This gives 21 g of a brown solid of melting point: 218° to 222° C, which is purified by boiling with toluene.

19.3 g of 4-hydroxyanthrone (which corresponds to a yield of 91.8% of the theoretical conversion), melting point: 220° to 223° C; purity: 95.8%.

EXAMPLE 3

10.5 g (50 mmols) of 11-H-dibenz[b,e]oxepin-6-one are added to 6.7 g (50 mmols) of aluminum trichloride in 20 ml of chlorobenzene at room temperature. The addition proceeds exothermically. The reaction mixture is then boiled at the reflux temperature one hour. The cooled mixture is hydrolysed with 5% strength hydrochloric acid and the product which has precipitated is filtered off.

Yield: 10.5 g of 4-hydroxyanthrone (which corresponds to a yield of 100% of the theoretical conversion), melting point: 232° to 234° C; purity 98.7%.

EXAMPLE 4

1st Reaction Stage 20.5 g (0.1 mol) of (2-chloro-methyl)-phenyl chloroformate are added dropwise to 57 g (0.3 mol) of titanium-IV chloride in 106 g (1 mol) of m-xylene at 115° C. The mixture is hydrolysed with 5% strength hydrochloric acid, washed with water until neutral and dried over sodium sulphate and the solvent is distilled off.

After the distillation in vacuo, 18 g (yield 65.5%) of a reaction product are obtained, which consists to the extent of 79% of 2-(2', 4'-dimethylbenzyl) and to the extent of 21% of 2-(3', 5'-dimethylbenzyl)-phenyl chloroformate. 2nd reaction stage 5 g (18.2 mmols) of the reaction product in stage 1 are boiled under reflux in 20 ml of dichlorobenzene with 3 g of aluminum trichloride for 30 minutes. On hydrolysing with 5% strength hydrochloric acid a solid precipitates which consists to the extent of 91% of 2,4-dimethyl-5-hydroxyanthrone and to the extent of 7% of 1,3-dimethyl-5-hydroxyanthrone.

Yield: 3.5 g of 1,3- and 2,4-dimethyl-5-hydroxyanthrone (which corresponds to a yield of 81% of the theoretical conversion).

EXAMPLE 5

1st Reaction Stage 105 g (0.5 mol) of 2-chloromethylphenyl chloroformate are warmed to 40° C with 195 g (2.5 mols) of benzene in 100 ml of hydrogen fluoride for one hour and to 100° C for a further hour. After distillation in vacuo, 60 g (yield: 52%) of 2-benzylphenyl fluoroformate are obtained. 2nd reaction stage 4.1 g (30 mmols) of aluminum trichloride and 6.9 g (30 mmols) of 2-benzylphenyl fluoroformate are stirred at 80° to 90° C until the evolution of gas has ended. The cooled mixture is hydrolysed with 5% strength hydrochloric acid and toluene is added. The solid which precipitates is filtered off and dried. This gives 2.5 g of 4-hydroxyanthrone (which corresponds to a yield of 40%, relative to the theoretical conversion).

Melting point: 230° to 233° C.

EXAMPLE 6

26.7 g (0.2 mol) of aluminum trichloride in 100 ml of nitromethane and 78 g (1 mol) of benzene are initially introduced and 20.5 g (0.1 mol) of 2-chloromethylphenyl chloroformate are added dropwise in the course of 20 minutes. The reaction proceeds exothermically and with vigorous evolution of gas. The mixture is subsequently allowed to react for 64 hours at 45° C. On hydrolysing with ice/hydrochloric acid, 14 g of 4-hydroxyanthrone precipitate (which corresponds to a yield of 66%, relative to the theoretical conversion).

Melting point: 220°–221° C
Purity: 94.5%.

EXAMPLE 7

1st Reaction Stage 239.5 g (1 mol) of 6-chloro-2-chloromethyl-phenyl chloroformate are added dropwise to 1.33 g (10 mmols) of aluminum trichloride in 780 g (10 mols) of boiling benzene in the course of 2 hours. After the evolution of gas has ended, the mixture is subsequently allowed to react for a further 1 hour and hydrolysed with 5% strength hydrochloric acid, and the organic phase is separated off and dried over sodium sulphate. After boiling off the solvent, the residue is distilled in vacuo.

This gives 176 g (0.63 mol) of 2-benzyl-6-chloro-phenyl chloroformate (which corresponds to a yield of 63%, relative to the theoretical conversion);

Boiling point$_{0.4}$ 143°–155° C
Purity: 95.5% pure.

2nd Reaction Stage (a) Without Solvent

A mixture of 28 g (0.1 mol) of 2-benzyl-6-chlorophenyl chloroformate and 13.5 g (0.1 mol) of aluminum trichloride is warmed carefully to 85°–90° C for 75 minutes. After cooling, product is taken up in chlorobenzene. On hydrolysing with 5% strength hydrochloric acid, 26 g of solid precipitate, which are recrystallised from chlorobenzene.

This gives 23 g (0.094 mol) of 3-chloro-4-hydroxyanthrone (which corresponds to a yield of 94%, relative to the theoretical conversion).

(b) In chlorobenzene 28 g (0.1 mol) of 2-benzyl-6-chloro-phenyl chloroformate and 13.5 g (0.1 mol) of aluminum trichloride are stirred in 50 ml of chlorobenzene for 40 minutes at 100° C. On hydrolysing the cooled solution with 5% strength hydrochloric acid, the product precipitates.

This gives 18 g (0.0735 mol) of 3-chloro-4-hydroxyanthrone (which corresponds to a yield of 73.5%, relative to the theoretical conversion). Melting point 186°–8° C.

EXAMPLE 8

1st Reaction Stage 41 g (0.2 mol) of 2-chloromethylphenyl chloroformate and 106 g (1 mol) of p-xylene in 100 ml of hydrofluoric acid are stirred for 1 hour at 60° C and for 1 hour at 100° C (final pressure 12 bars). The excess hydrofluoric acid is stripped off in vacuo at room temperature. The residue is taken up in methylene chloride and the methylene chloride solution is washed twice with water. After distilling off the solvent, the residue is distilled over a column in vacuo.

Boiling point$_{14}$: 174°–8° C.

Yield: 31 g of 2-(2′, 5′-dimethyl-benzyl)-phenyl fluoroformate (which corresponds to a yield of 60%, relative to the theoretical conversion).

2nd Reaction Stage 13 g (50.3 mmols) of the 2-(2′, 5′-dimethylbenzyl)-phenyl fluoroformate prepared in the first reaction stage are initially introduced in 50 ml of chlorobenzene and 6.8 g (51 mmols) of aluminum trichloride was added. The reaction mixture is boiled under reflux for 1 hour. On hydrolysing with 5% strength hydrochloric acid, 11 g of 1,4-dimethyl-5-hydroxyanthrone precipitate (which corresponds to a yield of 91.5%, relative to the theoretical conversion).

EXAMPLE 9

20.5 g (0.1 mol) of 2-chloromethyl-phenyl chloroformate are added dropwise to 135 mg (1 mmol) of aluminum trichloride in 106 g (1 mol) of boiling p-xylene. The mixture is subsequently allowed to react for one hour at 126° C. 13.5 g (0.1 mol) of aluminium trichloride and 100 ml of o-dichlorobenzene are added to the reaction mixture, cooled to 60° C. The excess p-xylene is distilled out of the reaction mixture up to 160° C. On hydrolysing with 5% strength hydrochloric acid, a solid precipitates and is filtered off. This solid is boiled with 5% strength hydrochloric acid.

This gives 21 g of 1,4-dimethyl-5-hydroxyanthrone (which corresponds to a yield of 88%, relative to the theoretical conversion).

Melting point: 172°–8° C.
Purity: 95.6%.

EXAMPLE 10

100 ml of hydrofluoric acid are added dropwise to 21 g (0.1 mol) of 11-H-dibenz[b,e]oxepin-6-one at 15° C. An inert gas pressure of 2 bars is applied to the solution with nitrogen and the autoclave is warmed. The mixture is allowed to react for one hour at 60° C and under a pressure of 2.7–2.9 bars and cooled, and the hydrofluoric acid is distilled off in vacuo up to 60° C.

This gives 20 g of 4-hydroxyanthrone (which corresponds to a yield of 95%, relative to the theoretical conversion).

Melting point: 230°–5° C

Purity: 99.2%.

EXAMPLE 11

(in analogy to German Pat. No. 932,924)

A mixture of 24.5 g of 3-chloro-4-hydroxyanthrone and 10 g of glyoxal sulfate is added in small portions within 2 hours to a mixture of 200 g of pyridine and 2 g of piperidine at 105° to 110° C and then stirred at this temperature 4 hours. After cooling the precipitated crystals are filtered off with suction and washed with alcohol. The product is boiled out twice with nitrobenzene. From the nitrobenzene filtrates crystallizes after a longer standing a blue dyestuff which is purified by recrystallization from ortho-dichlorobenzene.

From a blue vat cotton is dyed in a blue colour which has very high boiling and bleaching resistance against soda and chlorine.

What is claimed is:

1. A process for preparing a 4-hydroxyanthrone of the formula

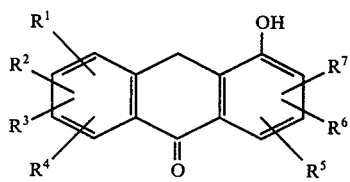

wherein $R^1$ to $R^7$ are the same or different and denote hydrogen, hydroxyl, halogen, cyano, $C_1$–$C_4$ alkyl, $C_1$–$C_4$ alkoxy, $C_1$–$C_4$ alkoxy, $C_1$–$C_4$ alkylmercapto, $C_1$–$C_4$ alkylsulphonyl, trifluoromethyl, trichloromethyl or an amino group of the formula

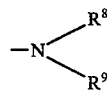

wherein $R^8$ and $R^9$ are identical or different and represent hydrogen, $C_1$–$C_4$ alkyl or $C_1$–$C_4$ alkylcarbonyl which comprises contacting a (2-halogenomethyl)-phenyl haloformate of the formula

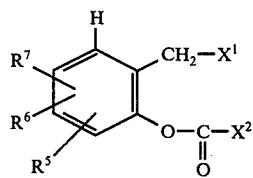

wherein $R^5$ to $R^7$ have the meanings indicated above and $X^1$ and $X^2$ are identical or different and represent a halogen with an aromatic carbocyclic compound of the formula

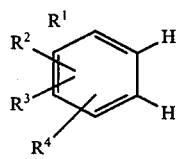

wherein $R^1$ to $R^4$ have the meanings indicated above, in the presence of a Friedel-Crafts catalyst at a temperature in the range of from 0° to 300° C.

2. A process according to claim 1 wherein the reaction is performed in the presence of a solvent.

3. A process according to claim 1 wherein the Friedel-Crafts catalyst is aluminum chloride or hydrogen fluoride.

4. A process according to claim 2 wherein the solvent is chlorobenzene or nitromethane.

5. A process according to claim 1 wherein:

A. in a first stage a 2-benzylphenyl haloformate of the formula

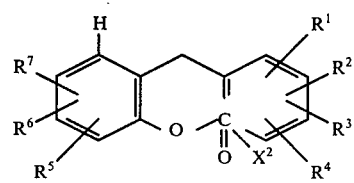

wherein $R^1$ to $R^7$ and $X^2$ have the above-described meaning is formed by contacting at 0° to 100° C a (2-halogeno-methyl)-phenyl haloformate of the formula

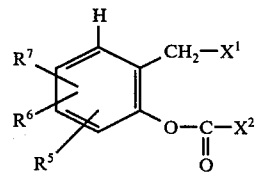

wherein $R^5$ to $R^7$ have the above-described meaning, with an aromatic carbocyclic compound of the formula

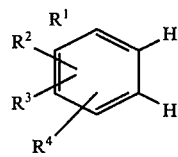

wherein $R^1$ to $R^4$ have the above-described meaning;

B. in a second stage said 2-benzylphenyl haloformate is converted to an 11-H-dibenz[b,e]oxepin-6-one of the formula

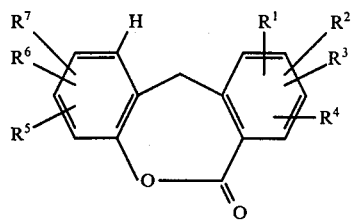

wherein $R^1$ to $R^7$ have the above described meaning by contacting the same with a Friedel-Crafts catalyst at a temperature from 20° to 120° C; and C. converting the resultant 11-H-dibenz[b,e]oxepin-6-one to a 4-hydroxyanthrone by contacting the same with a Friedel-Crafts catalyst at a temperature in the range of from 20° to 300° C.

6. A process for preparing a 4-hydroxyanthrone of the formula

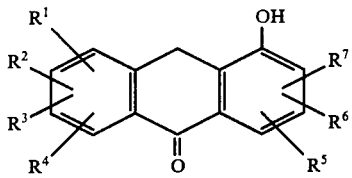

wherein $R^1$ to $R^7$ are identical or different and denote hydrogen, hydroxyl, halogen, cyano, $C_1$-$C_4$ alkyl, $C_1$-$C_4$ alkoxy, $C_1$-$C_4$ alkylmercapto, $C_1$-$C_4$ alkylsulphonyl, trifluoromethyl, trichlormethyl or an amino group of the formula

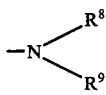

wherein $R^8$ and $R^9$ are identical or different and represent hydrogen, $C_1$-$C_4$ alkyl or $C_1$-$C_4$ alkylcarbonyl, which comprises contacting a compound of the formula

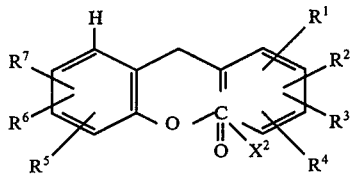

wherein $R^1$ to $R^7$ have the above-described meaning and $X^2$ represents halogen, with a Friedel-Crafts catalyst at a temperature between 20° and 300° C.

7. A process for preparing a 4-hydroxyanthrone of the formula

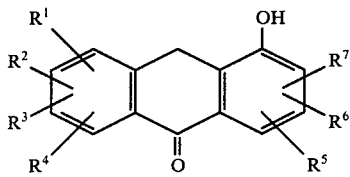

wherein $R^1$ to $R^7$ are identical or different and denote hydrogen, hydroxyl, halogen, cyano, $C_1$-$C_4$ alkyl, $C_1$-$C_4$ alkoxy, $C_1$-$C_4$ alkylmercapto, $C_1$-$C_4$ alkylsulphonyl, trifluoromethyl, trichloromethyl or an amino group of the formula

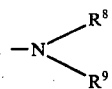

wherein $R^8$ and $R^9$ are identical or different and represent hydrogen, $C_1$-$C_4$ alkyl or $C_1$-$C_4$ alkylcarbonyl, which comprises contacting an 11-H-dibenz[b,e]oxepin-6-one of the formula

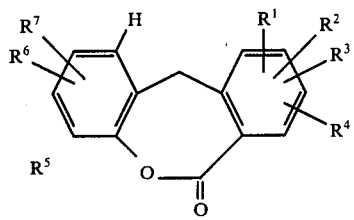

wherein $R^1$ to $R^7$ have the above-described meaning, with a Friedel-Crafts catalyst at a temperature between 20° and 300° C.

8. A 4-hydroxyanthrone of the formula

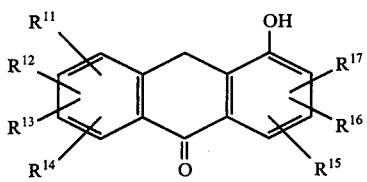

wherein $R^{11}$ to $R^{17}$ are identical or different and denote hydrogen, hydroxyl, fluorine, chlorine, bromine, cyano, $C_1$-$C_4$ alkyl, $C_1$-$C_4$ alkoxy, $C_1$-$C_4$ alkylmercapto, $C_1$-$C_4$ alkylsulphonyl, trifluoromethyl, trichloromethyl or an amino group of the formula

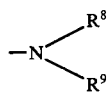

wherein $R^8$ and $R^9$ are identical or different and represent hydrogen, $C_1$-$C_4$ alkyl or $C_1$-$C_4$ alkylcarbonyl, at least one of the radicals $R^{11}$ to $R^{17}$ being different from hydrogen or methyl.

9. A compound according to claim 8 which is 3-chloro-4-hydroxyanthrone.

10. A compound according to claim 8 which is 1,4-dimethyl-5-hydroxyanthrone.

* * * * *

UNITED STATES PATENT AND TRADEMARK OFFICE
CERTIFICATE OF CORRECTION

PATENT NO. : 4,107,186

DATED : August 15, 1978

INVENTOR(S) : Petruck et al.

It is certified that error appears in the above-identified patent and that said Letters Patent are hereby corrected as shown below:

[57] Title Page, Abstract, line 1, "4-Novel" should read -- Novel-4 --.

[57] Abstract, first line after formula VIII, "$R^{11}$ and $R^{12}$" should read -- $R^{11}$ to $R^{12}$ --.

Column 8, line 32, "was" should read -- are --.

Signed and Sealed this

Tenth Day of April 1979

[SEAL]

Attest:

RUTH C. MASON
Attesting Officer

DONALD W. BANNER
Commissioner of Patents and Trademarks